(12) United States Patent
Lutz et al.

(10) Patent No.: US 8,377,062 B2
(45) Date of Patent: Feb. 19, 2013

(54) THERAPEUTIC AGENT CAPSULE FOR IMPLANTS

(75) Inventors: Christian Lutz, Mönkeberg (DE); Tim Bargen, Kiel (DE)

(73) Assignee: Stryker Trauma GmbH (DE)

( * ) Notice: Subject to any disclaimer, the term of this patent is extended or adjusted under 35 U.S.C. 154(b) by 49 days.

(21) Appl. No.: 12/640,774

(22) Filed: Dec. 17, 2009

(65) Prior Publication Data

US 2011/0150962 A1    Jun. 23, 2011

(51) Int. Cl.
*A61B 17/56*    (2006.01)
(52) U.S. Cl. .......................................................... 606/62
(58) Field of Classification Search ............... 604/890.1; 606/62, 64, 92; 623/17.12, 20.16, 20.17, 623/23.27, 23.26, 23.46, 23.48; 424/448, 424/451; 411/82.3; 29/525.13
See application file for complete search history.

(56) References Cited

U.S. PATENT DOCUMENTS

| | | | |
|---|---|---|---|
| 4,514,125 A | 4/1985 | Stol | |
| 4,919,666 A | 4/1990 | Buchhorn et al. | |
| 5,084,050 A | 1/1992 | Draenert | |
| 5,433,718 A | 7/1995 | Brinker | |
| 5,618,286 A | 4/1997 | Brinker | |
| 5,681,289 A | 10/1997 | Wilcox et al. | |
| 5,756,127 A | 5/1998 | Grisoni et al. | |
| 5,776,194 A | 7/1998 | Mikol et al. | |
| 6,048,343 A | 4/2000 | Mathis et al. | |
| 6,296,645 B1 | 10/2001 | Hover et al. | |
| 6,565,572 B2 | 5/2003 | Chappius | |
| 6,679,890 B2 | 1/2004 | Margulies et al. | |
| 6,709,436 B1 | 3/2004 | Hover et al. | |
| 6,783,529 B2 | 8/2004 | Hover et al. | |
| 6,786,908 B2 | 9/2004 | Hover et al. | |
| 7,160,302 B2 | 1/2007 | Warburton | |
| 7,488,320 B2 | 2/2009 | Middleton | |

(Continued)

FOREIGN PATENT DOCUMENTS

| | | |
|---|---|---|
| CN | 86209770 U | 11/1987 |
| CN | 1081872 A | 2/1994 |

(Continued)

OTHER PUBLICATIONS

Partial European Search Report, EP 10194802, dated Apr. 11, 2011.

(Continued)

*Primary Examiner* — Nicholas Lucchesi
*Assistant Examiner* — Brooke Matney
(74) *Attorney, Agent, or Firm* — Lerner, David, Littenberg, Krumholz & Mentlik, LLP

(57) ABSTRACT

The present invention discloses a system for releasing one or more therapeutic agents contained within a capsule onto or into an implant. At least one capsule is inserted in a recess preferably located along a longitudinal axis of the implant. The at least one adhesive capsule may be inserted in the recess and held in place therein by a holder. A plurality of adhesive capsules and holders may be inserted in one or more recesses located substantially along the longitudinal axis of the implant. The at least one capsule preferably has a casing housing one or more therapeutic agents, wherein the capsule is configured to be pierced by the at least one fastener to release the one or more therapeutic agents. The casing of the capsule may form an annular passageway to receive a guide wire for aiding the insertion of the capsule in an implant having a longitudinal bore along at least a portion thereof.

24 Claims, 8 Drawing Sheets

U.S. PATENT DOCUMENTS

| | | |
|---|---|---|
| 2001/0021852 A1 | 9/2001 | Chappius |
| 2002/0029041 A1 | 3/2002 | Hover et al. |
| 2002/0173792 A1 | 11/2002 | Severns et al. |
| 2003/0083662 A1 | 5/2003 | Middleton |
| 2004/0158252 A1 | 8/2004 | Prager et al. |
| 2004/0180072 A1 | 9/2004 | Tunc et al. |
| 2005/0149022 A1 | 7/2005 | Shaolian et al. |
| 2006/0229617 A1 | 10/2006 | Meller et al. |
| 2006/0247642 A1 | 11/2006 | Stone et al. |
| 2007/0083265 A1 | 4/2007 | Malone |
| 2007/0265704 A1 | 11/2007 | Mayer et al. |
| 2008/0021474 A1 | 1/2008 | Bonutti et al. |
| 2008/0039845 A1 | 2/2008 | Bonutti et al. |
| 2008/0039854 A1 | 2/2008 | Rabiner |
| 2008/0287949 A1 | 11/2008 | Keith et al. |
| 2009/0024161 A1 | 1/2009 | Bonutti et al. |
| 2009/0157078 A1 | 6/2009 | Mikol |
| 2009/0164016 A1 | 6/2009 | Georgy et al. |
| 2009/0204117 A1 | 8/2009 | Middleton |

FOREIGN PATENT DOCUMENTS

| | | |
|---|---|---|
| CN | 1826086 A | 8/2006 |
| CN | 201263717 Y | 7/2009 |
| CN | 102100943 A | 6/2011 |
| WO | 8801160 A1 | 2/1988 |
| WO | 9403143 A1 | 2/1994 |
| WO | 97/17032 A1 | 5/1997 |
| WO | 98/46169 A1 | 10/1998 |
| WO | 01/39812 A1 | 6/2001 |
| WO | 03/105698 A2 | 12/2003 |
| WO | 2004/096067 A2 | 11/2004 |
| WO | 2005020830 A1 | 3/2005 |
| WO | 2006/044490 A2 | 4/2006 |

OTHER PUBLICATIONS

European Search Report, EP 10194804, dated Mar. 10 11, 2011.
European Search Report, EP 10194802, dated Jun. 8, 2011.
Chinese Office Action with Search Report for Application No. 201010599704.7 dated Aug. 1, 2012.

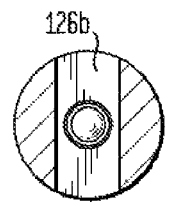
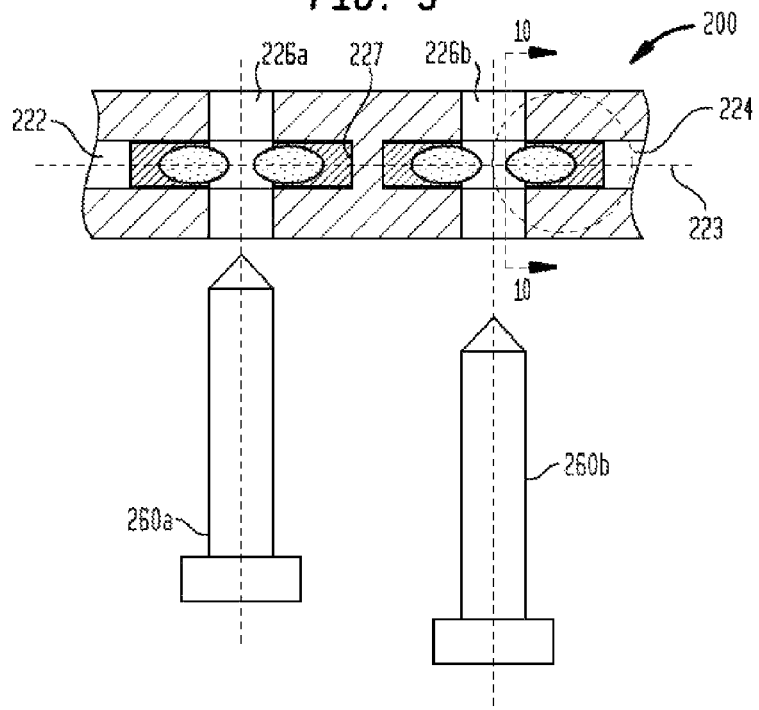
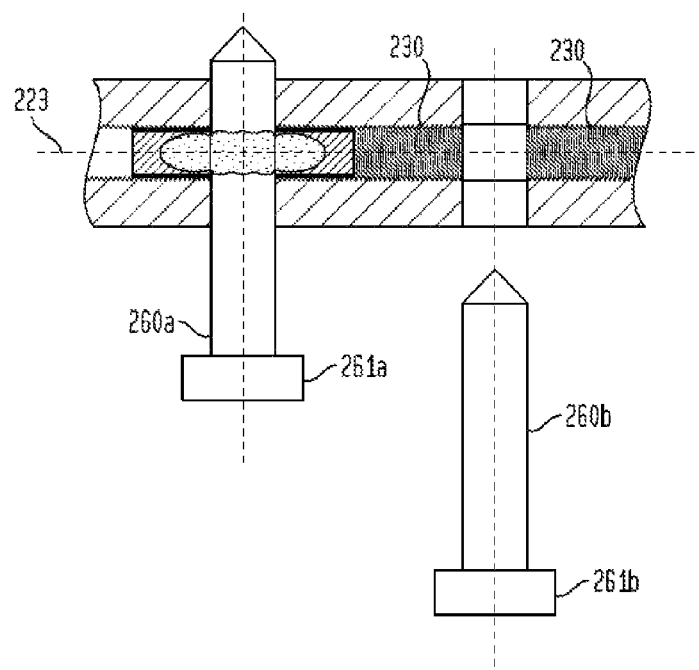

THERAPEUTIC AGENT CAPSULE FOR IMPLANTS

FIELD OF THE TECHNOLOGY

The present invention relates to a system and method for releasing a therapeutic agent at a surgical site and in or on an orthopedic implant, such as an intramedullary nail. In particular, the present invention relates to providing the therapeutic agent inside a capsule located adjacent a fastener receiving aperture in the implant and piercing the capsule with a fastener such that therapeutic agent inside the capsule is released.

BACKGROUND OF THE INVENTION

One or more therapeutic agents may be applied to or together with an orthopedic implant to aid in fighting infection, for example, at a surgical site. Such agents are generally applied to or somehow in connection with an implant prior to its implantation in or on the body of a patient, but may be applied after implantation.

Prior to implantation of an implant, a therapeutic agent such as an antibiotic may be spray coated onto the outside surface of the implant. The amount of antibiotic, the location in or on the implant that the antibiotic is applied to, and the velocity of the antibiotic spray, for example, is generally determined prior to the implant being sprayed with the antibiotic. By altering these factors, the therapeutic effect of the agent may also be altered. The implant may instead be dipped in a bath of the antibiotic, for example, such that the antibiotic may be quickly and easily applied to the inner and outer surfaces of the implant. One or more therapeutic agents may be applied to the implant in layers, perhaps via the aforementioned spray or bath, or may instead be combined to form a solution or compound that may be applied to the implant.

After implantation of an implant, a therapeutic agent such as an antibiotic may be supplied to the surgical site or onto the implant itself through a fastener, such as a bone screw. In such a case, the fastener may be sprayed or bathed, for example, with the antibiotic prior to being used to secure the implant at a specific location in or on the body of the patient.

Some therapeutic agents whether applied directly to an implant or introduced to the surgical site via a fastener, are time released, such that a predetermined amount of the therapeutic agent may provided to the surgical site at generally specific time intervals. In such a case, the therapeutic agent may be applied to the implant prior to its implantation in or on the body of the patient, and then may be released to provide a therapeutic effect to the surgical site after it has been implanted 12 hours, for example. A portion of the therapeutic agent applied to the implant may be released at that 12 hour time period, while one or more portions of the therapeutic agent may then be released at one or more later times.

Implants may alternatively be provided with internal reservoirs housing one or more therapeutic agents. The agents inside the reservoirs are generally released to the surgical site after the implant is implanted in or on the body of the patient. The therapeutic agent may seep out of the reservoir, for example, through a small opening in the reservoir regulating the release of the agent.

BRIEF SUMMARY OF THE INVENTION

A first aspect of the invention is a system for releasing a material at a surgical site including an implant having at least one recess therein, a capsule having a casing housing the material, the capsule adapted to be received within the at least one recess of the implant, and a piercing member having a end portion, wherein the end portion of the piercing member is configured to pierce the casing of the capsule to release the material housed therein.

In accordance with one embodiment of this first aspect of the present invention, the piercing member is a fastener. In another embodiment, the fastener may be a bone screw.

In accordance with another embodiment of this first aspect of the present invention, the material includes a therapeutic agent. In another embodiment, the material further includes an adhesive adapted to secure the piercing member in the at least one recess of the implant upon the adhesive hardening after first being released from the capsule.

A second aspect of the present invention is an implant for housing a therapeutic capsule including an elongate shaft having a longitudinal bore at least partially therethrough and first and second bone screw receiving apertures. Preferably, the apertures each extend transverse to the longitudinal bore. The therapeutic capsule having a casing housing a therapeutic agent is positioned within the bore and preferably communicates with both the first and second apertures.

In accordance with one embodiment of this second aspect of the present invention, the implant further includes a holder adapted to be received within the longitudinal bore of the elongate shaft, the holder adapted to receive the therapeutic capsule therein and position the capsule at least partially within the first and second apertures such that the capsule communicates with both the first and second apertures.

In accordance with another embodiment of this second aspect of the present invention, the implant further includes a holder adapted to be received within the longitudinal bore of the elongate shaft, wherein the holder has a first and a second end, each end having a recess for holding a therapeutic capsule to position the capsule at least partially within either the first or the second apertures.

In accordance with yet another embodiment of this second aspect of the present invention, the longitudinal bore is threaded adjacent the nail aperture and the holder is threaded and adapted to threadingly engage the longitudinal bore of the elongate shaft. In another embodiment, the therapeutic capsule may also include an adhesive.

In accordance with still yet another embodiment of this second aspect of the present invention, the implant includes a first therapeutic capsule and a second therapeutic capsule, wherein the holder is adapted to receive both first and second therapeutic capsules therein and position the first capsule at least partially within the first aperture and the second capsule at least partially within the second aperture. In another embodiment, the first and second therapeutic capsules also each include an adhesive.

A third aspect of the present invention is a bone nail includes an elongate shaft having a longitudinal axis extending from a proximal end to a distal end of the shaft, the shaft having a plurality of fastener receiving apertures having an axis transverse to the longitudinal axis of the shaft, and at least one recess communicating with each fastener receiving aperture, wherein each recess has an axis preferably perpendicular to the longitudinal axis of the shaft. The bone nail further includes at least one therapeutic capsule having a casing housing a therapeutic agent, and a holder adapted to be received within at least partially within a recess of the elongate shaft, the holder having at least one recess adapted to receive the capsule and position the capsule at least partially within the at least one aperture. In another embodiment, the capsule also preferably includes an adhesive. In another embodiment, the holder is preferably cylindrical.

In accordance with one embodiment of this third aspect of the present invention, the holder is threaded and the at least on recess of the elongate shaft is threaded and the holder is adapted to threadingly engage the at least one recess.

In accordance with another embodiment of this third aspect of the present invention, the bone nail has first and second transverse apertures and the holder is positioned within the at least one recess such that the holder communicates with the first and second transverse apertures, the holder having first and second recesses each adapted to receive a capsule.

In accordance with yet another embodiment of this third aspect of the present invention, the bone nail further includes a first capsule positioned at least partially within the first transverse aperture and a second capsule positioned at least partially within the second transverse aperture. In another embodiment, the first and second capsules preferably each also include an adhesive.

A fourth aspect of the present invention is a method for regulating the release of a therapeutic agent to an implant. The method includes positioning the implant adjacent bone, the implant having at least one aperture for receiving an elongate fastener therein and an internal recess communicating with the aperture. The method further includes placing a therapeutic capsule within the internal recess, the capsule extending at least partially into the at least one aperture, the capsule having a casing housing the therapeutic agent, the casing configured to be pierced by a fastener. The method further include inserting the fastener through the at least one aperture, and piercing the capsule with at least a portion of the fastener such that the therapeutic agent is released from the capsule adjacent the location of the at least one aperture on the implant.

In accordance with one embodiment of this fourth aspect of the present invention, the implant is an intramedullary nail, and the recess is a longitudinal bore extending at least partially along a length of the intramedullary nail.

In accordance with another embodiment of this fourth aspect of the present invention, the method further includes placing a retaining ring around the casing of the capsule prior to piercing the capsule with the fastener, the retaining ring configured to aid in maintaining the position of the adhesive capsule within the longitudinal bore of the intramedullary nail.

In another embodiment, the implant has a plurality of apertures adapted to each receive an elongate fastener therein and an internal recess communicating with each aperture. The method further includes placing a capsule within the internal recess communicating with each aperture, wherein each capsule extends at least partially into each aperture.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 9 is a cross-sectional view of an alternative embodiment of an intramedullary nail having a plurality of holders and capsules shown in FIG. 7 located in a longitudinal bore of the intramedullary nail.

FIG. 10 is a cross-sectional view of the intramedullary nail taken along line B-B of FIG. 9.

FIG. 11 is a cross-sectional view of the intramedullary nail shown in FIG. 9, with one of the plurality of capsules having been pierced by a fastener located in an aperture of the intramedullary nail.

DETAILED DESCRIPTION

As used herein, when referring to bones or other parts of the body, the term "proximal" means closer to the heart and the term "distal" means more distant from the heart. The term "inferior" means toward the feet and the term "superior" means toward the head. The term "anterior" means toward the front part of the body or the face and the term "posterior" means toward the back of the body. The term "medial" means toward the midline of the body and the term "lateral" means away from the midline of the body.

Figure 1:
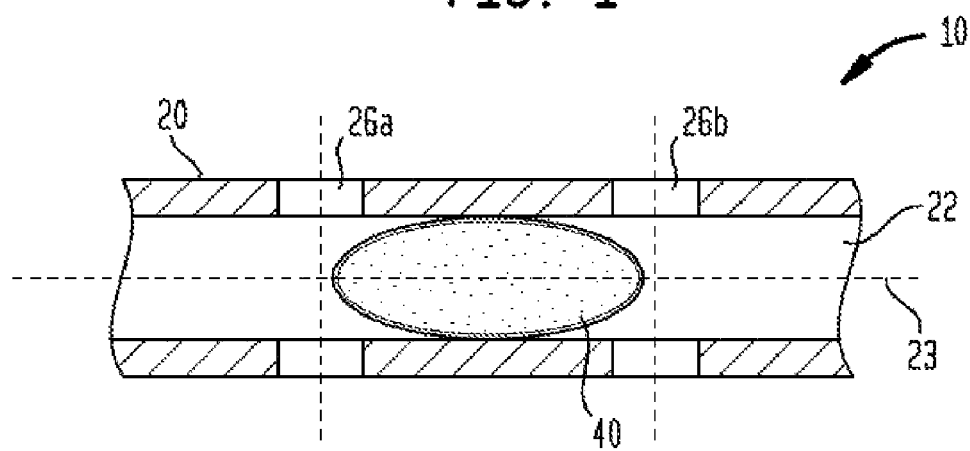
FIG. 1 is a cross-sectional view of an embodiment of a longitudinal bore of an intramedullary nail having a capsule located therein.
Figure 2:
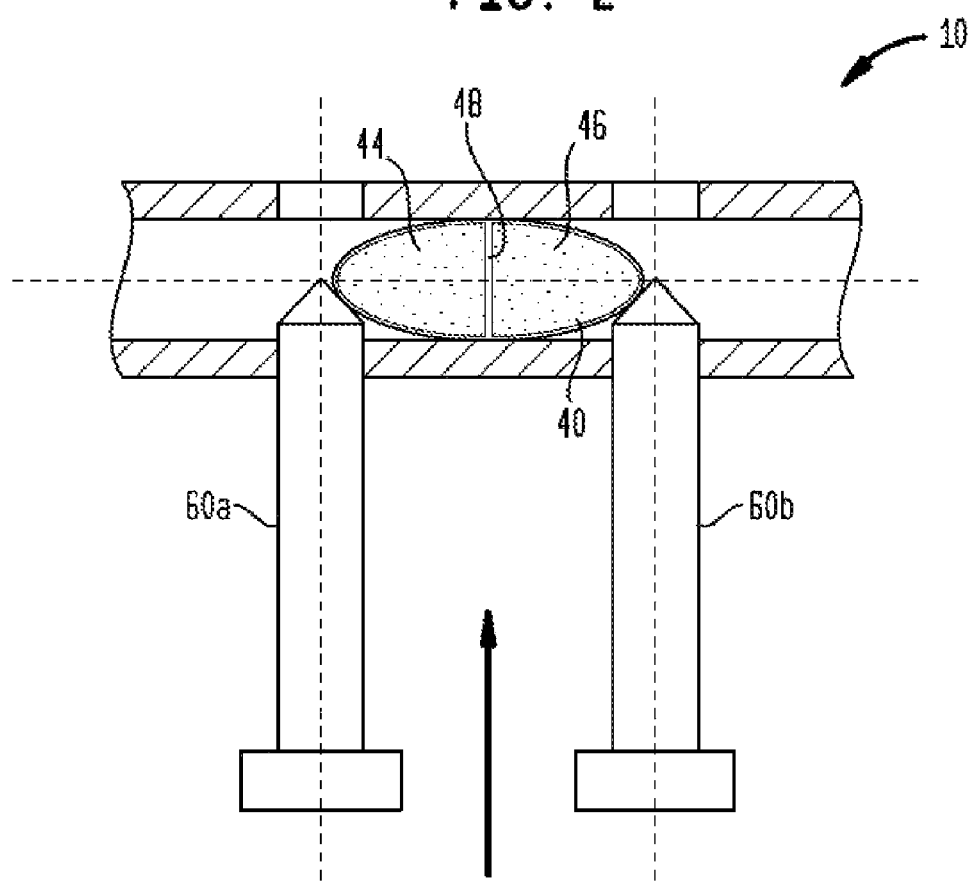
FIG. 2 is a cross-sectional view of the intramedullary nail shown in FIG. 1, with tips of two fasteners each located in an aperture of the intramedullary nail.
Figure 3:
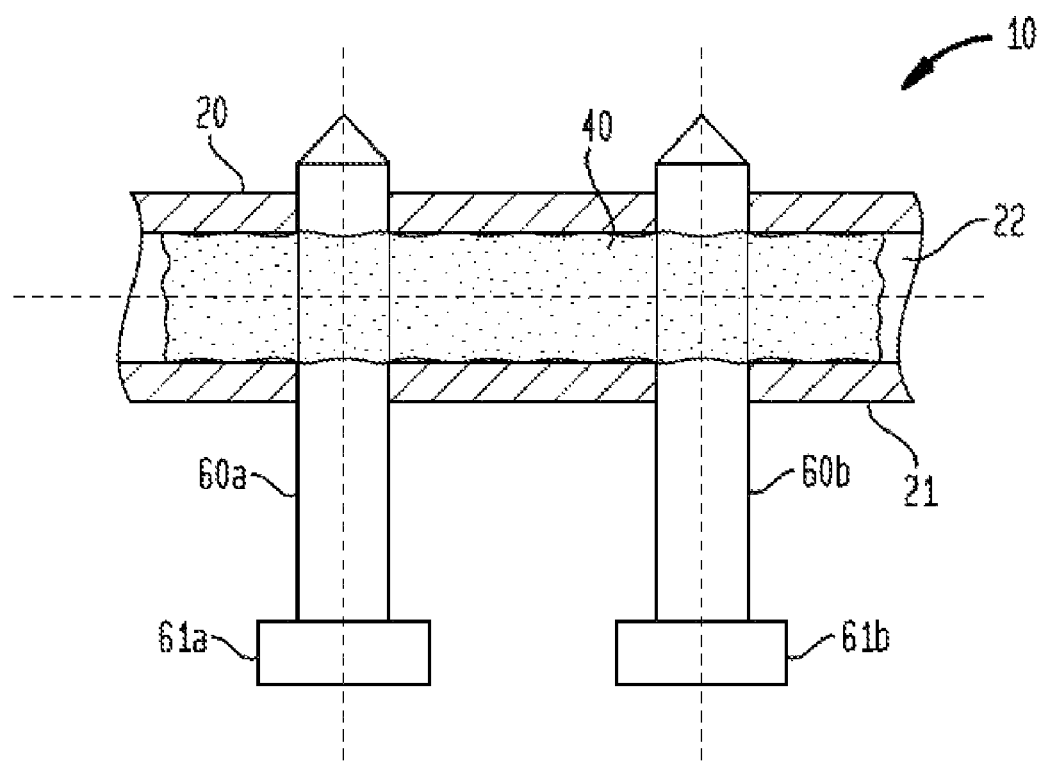
FIG. 3 is a cross-sectional view of the adhesive capsule, intramedullary nail, and two fasteners shown in FIG. 2, with the capsule having been pierced by the two fasteners.

Referring to the drawings, wherein like reference numerals represent like elements, there is shown in the figures, in accordance with embodiments of the present invention, a screw locking system, designated generally by reference numeral 10. FIGS. 1-3 refer to therapeutic agent releasing system 10. Preferably therapeutic agent releasing system 10 includes a portion of an implant, such as an intramedullary nail 20, at least one capsule 40 containing a therapeutic agent, and at least one fastener 60. Two fasteners 60a, 60b are shown in FIGS. 2 and 3.

While FIGS. 1-3 show the implant in therapeutic agent releasing system 10 as a portion of an intramedullary nail, therapeutic agent releasing system 10 may include any type of implant that may be implanted in or on the body of a patient. For example, therapeutic agent releasing system 10 may be provided in knee, hip, shoulder, or spine implants, for example. Preferably, therapeutic agent releasing system 10 may be provided in any implant where it would be beneficial to release a therapeutic agent at the surgical site.

Having the therapeutic agent contained within a capsule is an effective means in regulating the release of the therapeutic agent to a surgical site. For instance, a surgeon or any other operating room personnel may release the therapeutic agent contained within a capsule at a specific time during a surgical procedure by piercing the capsule. Preferably, the capsule is pierced by a fastener that is configured to secure the implant to the surgical site. The capsule may be pierced using other means such as with a pointed instrument. Also, the amount of therapeutic agent released may be predetermined by the size of the capsule. Based on the amount of therapeutic agent that may be beneficial for a certain implant and/or surgical site, the amount of therapeutic agent contained with the capsule or the number of capsules provided with the implant may be changed. Also, the flow rate of the therapeutic agent being released from the capsule may be regulated by the viscosity of the therapeutic agent contained within the capsule.

As shown in FIGS. 1-3, intramedullary nail 20 is preferably an elongate shaft configured to be housed within a canal of a patient's femur. Preferably, intramedullary nail 20 includes a longitudinal bore 22 at least partially along a length thereof. Bore 22 is shown having an axis 23. While axis 23 is shown as a straight line in FIGS. 1-3, axis 23 may curve if a portion of the length of nail 20 is also curved. Nail 20 preferably further includes at least first and second bone screw receiving apertures 26a, 26b. Preferably, apertures 26a, 26b each extend transverse to longitudinal bore 22 of intramedullary nail 20.

Capsule 40 preferably includes an outer casing housing a therapeutic agent. The outer casing of the adhesive capsule is preferably thin such that it may easily be pierced by fasteners, such as fasteners 60a, 60b, for example. As shown in FIG. 1, capsule 40 forms a chamber for housing a therapeutic agent therein. Alternatively, capsule may include two chambers 44, 46 as shown in FIG. 2, or more than two chambers. A barrier wall 48 separates of the therapeutic agent contained within capsule 40 into first and second chambers 44, 46. Capsule 40 may further include more than one barrier wall 48 to form a plurality of chambers. A first therapeutic agent may be contained in the first chamber 44 while a second therapeutic agent may be contained in the second chamber 46. Also, more the one therapeutic agent or a solution of compound of therapeutic agents may be contained in either first or second chambers 44, 46.

As shown in the embodiment of FIG. 2, capsule 40 is positioned within bore 22 and is communicating with both first and second apertures 26a, 26b. First chamber 44 and second chamber 46 of capsule 40 is separated by barrier wall 48. In this embodiment, first chamber 44 may be pierced by fastener 60A, for example, without second chamber 46 being pierced and vice versa.

As shown in FIG. 3, fasteners 60a, 60b have pierced capsule 40 such that a therapeutic agent preferably surrounds a length of fasteners 60a, 60b. Preferably, fasteners 60a, 60b are received within apertures 26a, 26b until heads 61a, 61b of each fastener 60a, 60b is seated on an exterior surface of the patient's bone (not shown). Depending on the chemical and/or physical properties of the therapeutic agent located inside capsule 40, the therapeutic agent will preferably surround fasteners 60a, 60b and may flow to other inner and outer surfaces of nail 20 and/or locations adjacent the surgical site.

Figure 4:
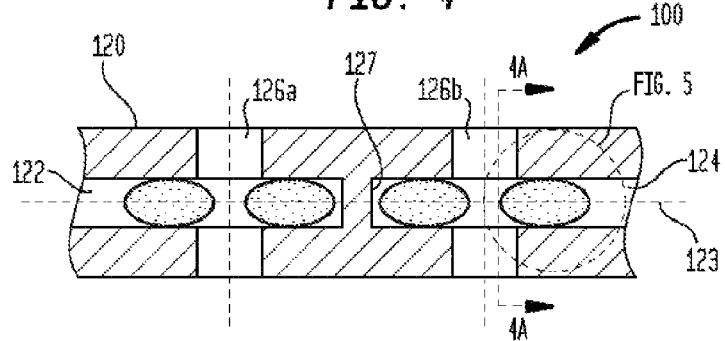
FIG. 4 is a cross-sectional view of an embodiment of an intramedullary nail, including a plurality of capsules each located in recesses adjacent apertures of the intramedullary nail.
Figure 5:
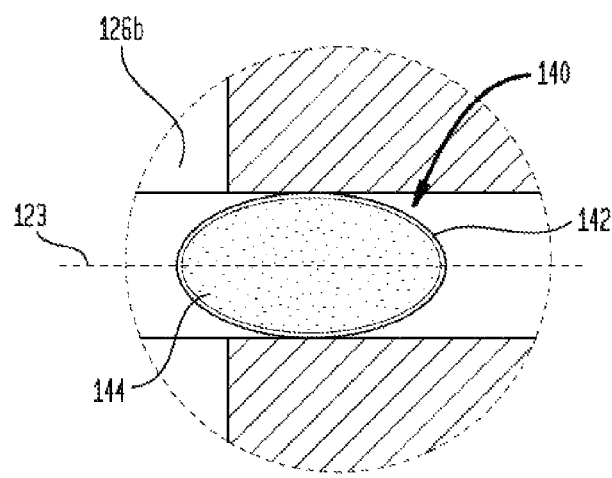
FIG. 5 is an embodiment of a capsule of the present invention.
Figure 6:
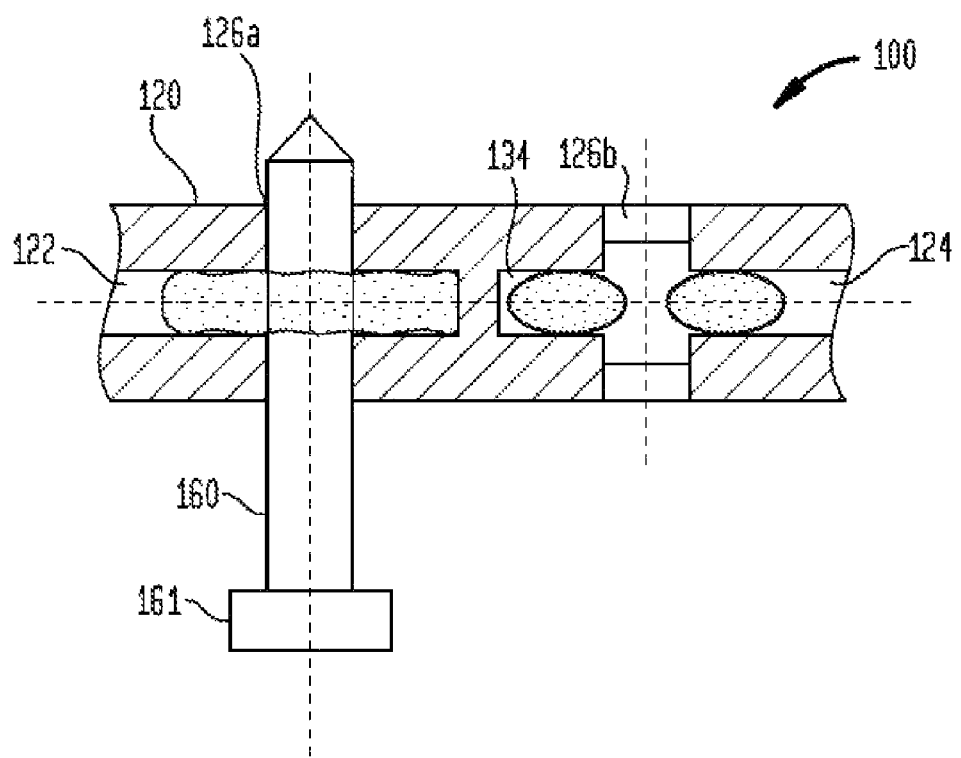
FIG. 6 is a cross-sectional view of the intramedullary nail shown in FIG. 4, with two of the plurality of capsules having been pierced by a fastener located in an aperture of the intramedullary nail.

FIGS. 4-6 refer to therapeutic agent releasing system 100. Preferably therapeutic agent releasing system 100 includes intramedullary nail 120, at least one capsule 140, and at least one fastener 160.

Intramedullary nail 120 is a preferably elongate shaft configured to be housed within a canal of a patient's femur. Preferably, intramedullary nail 120 includes at least two longitudinal recess or bores 122, 124 at least partially along a length thereof. In this embodiment, recess or bore 122 does not extend along a substantial length of nail 120, and is preferably interrupted by a wall 127 along the length of nail 120 separating recess 122 from recess 124. Preferably, each recess 122, 124 is shown having an axis 123. While axis 123 is shown as a straight line in FIGS. 4-6, axis 123 may curve if a portion of the length of nail 120 is also curved. Intramedullary nail 120 preferably further includes at least first and second bone screw receiving apertures 126a, 126b. Preferably, apertures 126a, 126b each extend transverse to longitudinal bore 122 of intramedullary nail 120.

Capsule 140 preferably includes an outer casing housing a therapeutic agent. The outer casing of the capsule is preferably thin such that it may easily be pierced by fasteners, such as fastener 160 for example. As shown in FIG. 5, capsule 140 forms chamber 144 for housing a therapeutic agent therein. Alternatively, capsule 140 may include two or more chambers. A barrier wall may be used to separate the therapeutic agent contained within capsule 140 into first and second chambers, for instance. Capsule 140 may further include more than one barrier wall to form a plurality of chambers.

Figure 4A:
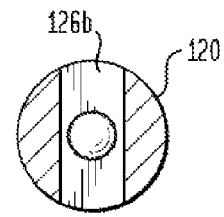
FIG. 4A is a cross-sectional view of the intramedullary nail taken along line A-A of FIG. 4.

As shown in FIG. 4, a plurality of capsules 140 are located in recesses 122, 124 of nail 120. Capsules 140 are located in recesses 122, 124 such that a portion of capsules 140 is located in fastener receiving apertures 126a, 126b of nail 120. FIG. 4A is a cross-sectional view showing capsule 140 located in recess 124, for example. FIG. 5 is a detailed view also showing capsule 140 located in recess 124, wherein a portion of capsule 140 is clearly shown located in fastener receiving apertures 126b of nail 120. Depending on the properties of the therapeutic agent contained within capsule 140 and the location of capsule 140 located in a fastener receiving aperture of nail 120 preferably determines how much therapeutic agent will come in contact with a fastener that pierces capsule 140 in the fastener receiving aperture of nail 120.

As shown in FIG. 6, fasteners 160 has pierced capsule 40 in fastener receiving aperture 126a such that the therapeutic agent preferably surrounds a length of fastener 160. Preferably, fastener 160 is received within apertures 126a, 126b until a head 161 of fastener 160 is seated on the exterior surface of the patient's bone (not shown). Depending on the chemical and physical properties of the therapeutic agent located inside capsule 140, the therapeutic agent will preferably surround fasteners 160a, 160b and may flow to other inner and outer surfaces of nail 120 and/or locations adjacent the surgical site.

FIGS. 7-11 refer to therapeutic agent releasing system 200. Preferably therapeutic agent releasing system 200 includes intramedullary nail 200, at least one capsule 240, at least one capsule holder 270, and at least one fastener 260. Two fasteners 260a, 260b are shown in FIG. 9. Therapeutic agent releasing system 200 may also include an insertion instrument 290 for engaging and manipulating capsule holder 270.

Figure 7:
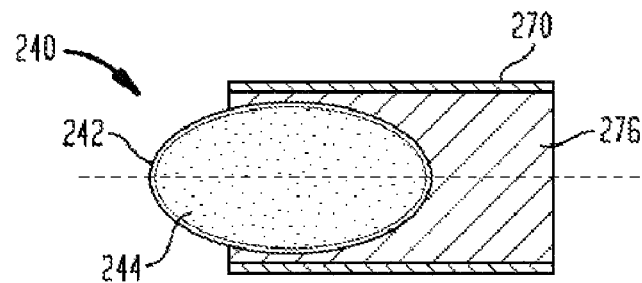
FIG. 7 is a cross-sectional view of an embodiment of a holder, including a capsule located partially within the holder.
Figure 8:
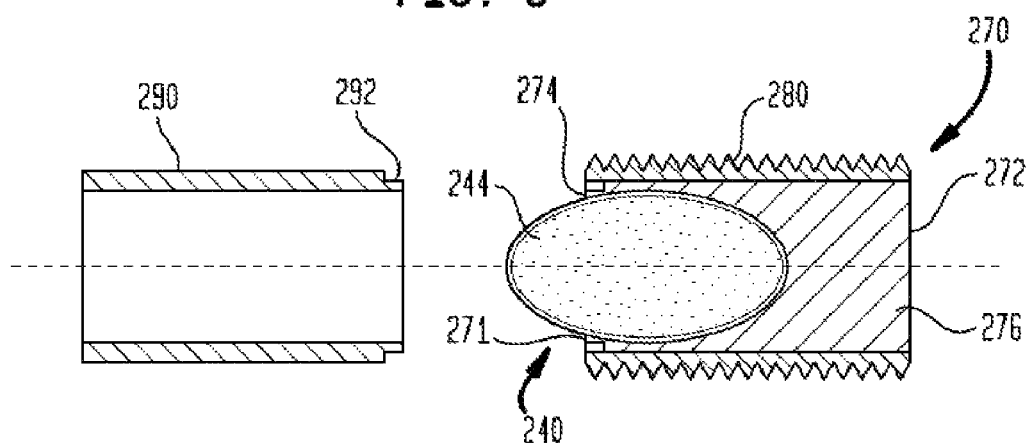
FIG. 8 is a cross-sectional view of the holder shown in FIG. 7, with an insertion instrument for engaging the holder.
Figure 8A:
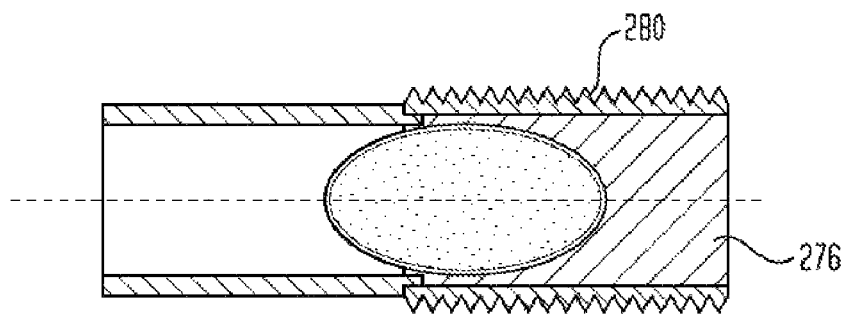
FIG. 8A is a view of the insertion instrument engaged to the holder shown in FIG. 8.
Figure 12:
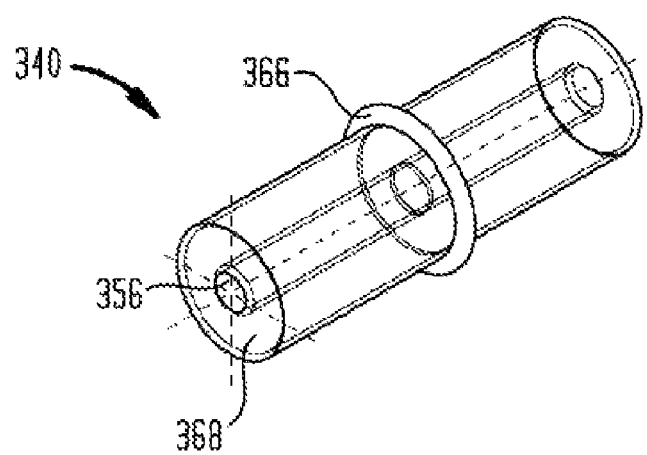
FIG. 12 is a perspective view of an alternative embodiment of a capsule.
Figure 13:
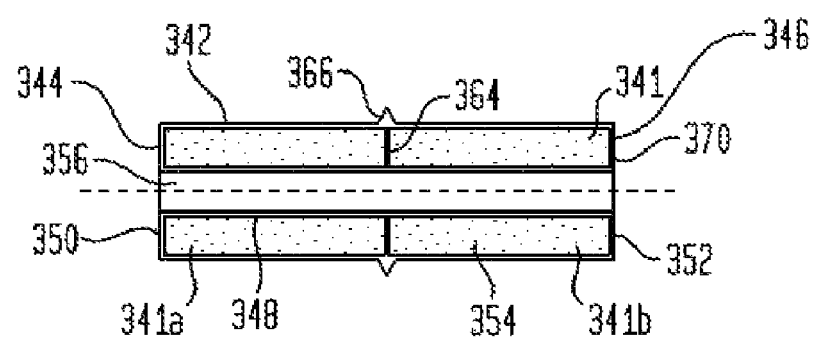
FIG. 13 is a cross-sectional view taken along the line C-C of the capsule shown in FIG. 12.

FIGS. 7-8A show capsule 240, capsule holder 270, and insertion instrument 290. As shown in FIG. 7, capsule 240 preferably includes an outer casing 242 housing a therapeutic agent. The outer casing 242 of the capsule 240 is preferably thin such that it may easily be pierced by fasteners, such as fasteners 260a, 260b as shown in FIG. 9, for example. Capsule 240 preferably forms chamber 244 for housing the therapeutic agent therein. Alternatively, capsule 240 may include two or more chambers. A barrier wall may be used to separate the therapeutic agent of capsule 240 into first and second chambers, for instance. Capsule 240 may further include more than one barrier wall to form a plurality of chambers.

In FIG. 8, insertion instrument 290 is shown in alignment with capsule holder 270 prior to being engaged to capsule holder 270 as shown in FIG. 8A. Insertion instrument 290 preferably has an engagement end 292 that is configured to engage a corresponding end 274 of capsule holder 270. The engagement between insertion instrument 290 and capsule holder 270 may occur through a press-fit, threaded engagement, or a lock-fit, such as a ball and detent connection, for example.

Holder 270 has first and second ends 271, 272, each end having a recess 276 for housing a capsule 240 therein. Recess 276 may be a bore that passes through first and second ends 271, 272 of holder 270. As shown in FIG. 8, holder 270 may include external threads 280 configured to engage corresponding threads in nail 220. Holder 270 is preferably cylindrical.

In therapeutic agent releasing system 200, intramedullary nail 220 is a preferably elongate shaft configured to be housed within a canal of a patient's femur. Preferably, intramedullary nail 220 includes at least two longitudinal recess or bores 222, 224 at least partially along a length thereof. In this embodiment, recess or bore 222 does not extend along a substantial length of nail 220, and is preferably interrupted by a wall 227 along the length of nail 220 separating recess 222 from recess 224. Preferably, each recess 222, 224 is shown having an axis 223. While axis 223 is shown as a straight line in FIGS. 9 and 11, axis 223 may curve if a portion of the length of nail 220 is also curved. Intramedullary nail 220 preferably further includes at least first and second bone screw receiving apertures 226a, 226b. Preferably, apertures 226a, 226b each extend transverse to recesses 222, 224 of intramedullary nail 220.

As shown in FIG. 9, a plurality of capsules 240 each housed in a holder 270 are located in recesses 222, 224 of nail 120. Holder 270 housing capsules 240 are located in recesses 222, 224 such that a portion of capsules 240 are located in fastener receiving apertures 226a, 226b of nail 220. FIG. 10A is a cross-sectional view showing capsule 240 located in recess 224, for example.

As shown in FIG. 11, fasteners 260a has pierced capsule 240 in fastener receiving aperture 226a such that the therapeutic agent that was contained therein now preferably surrounds a length of fastener 260a. Preferably, fastener 260a is received within apertures 226a until a head 261 of fastener 260a is seated on the exterior surface of the patient's bone (not shown). Depending on the chemical and physical properties of the therapeutic agent located inside capsule 240, the therapeutic agent will preferably surround fastener 260a, for example, and may flow to other inner and outer surfaces of nail 220 and/or locations adjacent the surgical site.

Recesses 222, 224 are shown threaded in FIG. 11, such that an insertion instrument 290 engaged to a holder 270 may be rotated to thread holder 270 into position within recesses 222, 224. Holder 270 is adapted to be received within a longitudinal bore 22, or recesses 122,124,222,224 of the elongate shaft of nail 10,100,200.

In one embodiment, nail 10 includes first and second transverse apertures 26a, 26b and holder 270 is positioned within the longitudinal bore 22 of nail 20 such that the holder 270 communicates with the first and second transverse apertures 26a, 26b, wherein the holder 270 has first and second recesses 272 each adapted to receive capsule 40,140,240.

FIGS. 12-15 refer to therapeutic agent releasing system 300. Preferably therapeutic agent releasing system 300 includes intramedullary nail 320, at least one capsule 340, and at least one fastener 360 (not shown).

Intramedullary nail 320 is a preferably elongate shaft configured to be housed within a canal of a patient's femur. Preferably, intramedullary nail 320 includes a longitudinal bore 322 at least partially along a length thereof. Longitudinal bore 322 preferably includes at least one recess 321 adapted to receive a retaining portion 366 extending from capsule 340. Intramedullary nail 320 preferably further includes at least first and second bone screw receiving apertures 326a, 326b. Preferably, apertures 326a, 326b each extend transverse to longitudinal bore 322 of intramedullary nail 320.

Capsule 340 preferably includes a longitudinally extending exterior wall 342 having a first end 344 and a second end 346. Capsule 340 preferably further includes a longitudinally extending interior wall 348 spaced from exterior wall 342, the interior wall 348 having a first end 350 and a second end 352. The first and second ends of the exterior and interior walls are preferably sealed, such that the sealed exterior and interior walls define an enclosed chamber 354. Preferably, therapeutic agent 341 is contained within enclosed chamber 354. The interior wall 348 forms a passageway 356 along a length of the capsule 340 and through the first and second ends 350, 352 of interior wall 348.

Figure 15:
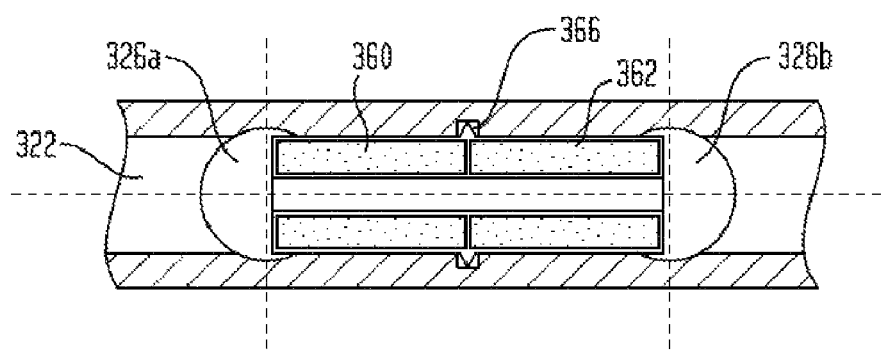
FIG. 15 is a cross-sectional view of the capsule located in the longitudinal bore of the intramedullary nail shown in FIG. 14.

As shown in FIG. 15, the enclosed chamber 354 containing therapeutic agent 341 preferably includes a first longitudinal section 360 and a second longitudinal section 362 separated by a barrier wall 364 such that the therapeutic agent in the first section 341a is separated from the therapeutic agent in the second section 342b. Preferably, barrier wall 364 is located at an intermediate portion along the length of capsule 340. Preferably, the exterior wall 342 of capsule 340 has a circumferential ridge or retaining portion 366 that extends outwardly therefrom.

Preferably, the exterior and interior walls 342, 348 of capsule 340 are substantially cylindrical and passageway 322 is substantially cylindrical such that the enclosed chamber 354 is annular.

Preferably, capsule 340 includes a first end wall 368 and a second end wall 370, wherein a first end of annular chamber 354 located at first ends 344, 350 of exterior and interior walls 342, 348 is sealed by the first end wall 368 and a second end of annular chamber 354 located at second ends 346, 352 of exterior and interior walls 342, 348 are sealed by second end wall 370.

Figure 14:
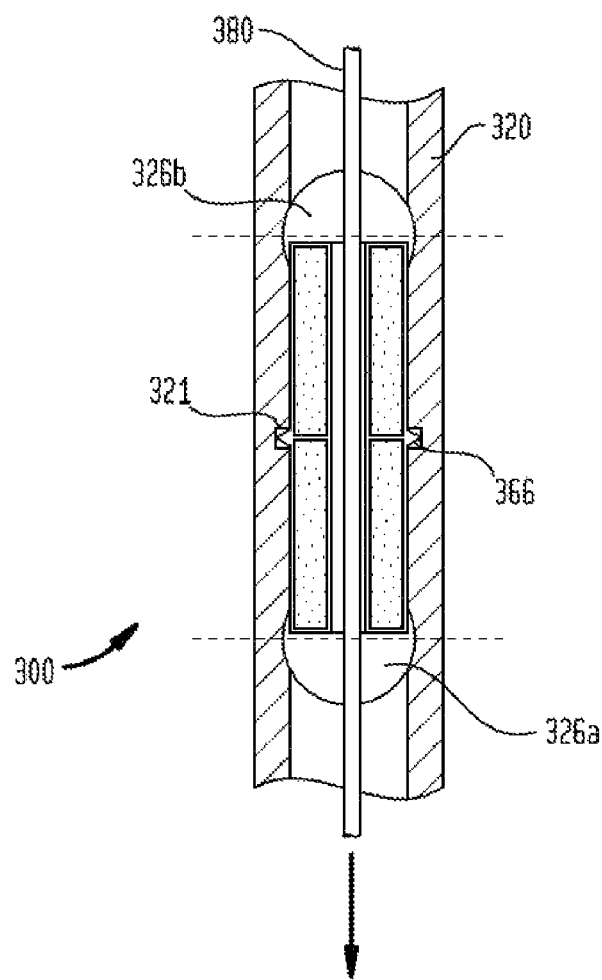
FIG. 14 is a perspective view of an intramedullary nail, guide wire, and capsule shown in FIG. 12.

As shown in FIGS. 14 and 15, in order to place capsule 340 in position within nail 320, a portion of a guide wire 380 is passed through passageway 356 of capsule 340. Guide wire 380 has a sufficient diameter to pass through passageway 356 while also allowing guide wire 380 to engage interior wall 348 of capsule 340. Once capsule 340 is engaged to guide wire 380, capsule 340 may be received in longitudinal bore 322 of nail 320. Preferably, guide wire 380 passes through longitudinal bore 322 of nail 320 until retaining ring 366 engages recess 323 of longitudinal bore 322 as shown in FIG. 14.

As shown in FIG. 15, once capsule 340 is in place, guide wire 380 may be removed from longitudinal bore 322 of nail 320 leaving behind capsule 340. Similar to the embodiment shown in FIG. 3, fasteners 360a, 360b (not shown) may be placed through apertures 326a, 326b of nail 320 respectively such that fasteners 360a, 360b pierce capsule 340. Preferably, after piercing capsule 340 with fasteners 360a, 360b, the therapeutic agent housed within annular chamber 341 preferably surrounds a length of fasteners 360a, 360b. Preferably, fasteners 360a, 360b are received within apertures 326a, 326b until a head 361 of each fastener is seated on an exterior surface of the patient's bone (not shown). Depending on the chemical and/or physical properties of the therapeutic agent located inside capsule 340, the therapeutic agent will preferably surround fasteners 360a, 360b, and may flow to other inner and outer surfaces of nail 320 and/or locations adjacent the surgical site.

Such therapeutic agents contained within capsules 40, 140, 240, 340, may be biologically active agents. Active agents amenable for use in capsules 40, 140, 240, 340 include growth factors, such as bisphosphonates, transforming growth factors, fibroblast growth factors, platelet derived growth factors, epidermal growth factors, connective tissue activated peptides, osteogenic factors, and biologically active analogs, fragments, and derivatives of such growth factors.

In addition to the biological active agents discussed above, a large number of pharmaceutical agents are known in the art and are amenable for use in capsule. The term "pharmaceutical agent" includes without limitation, medicaments, vitamins, mineral supplements, substances used for the treatment, prevention, diagnosis, cure or mitigation of disease or illness, or substances which affect the structure or function of the body, or prodrugs, which become biologically active or more active after they have been placed in a predetermined physiological environment.

Non-limiting examples of broad categories of useful pharmaceutical agents include the following therapeutic categories: anabolic agents, antacids, anti-asthmatic agents, anticoagulants, anti-convulsants, anti-diarrheals, anti-infective agents, anti-inflammatory agents, anti-nauseants, and analgesic agents.

The therapeutic agent may also be an at least one drug that is a member of a drug class selected from the group consisting of ace-inhibitors, alkaloids, anabolic agents, analgesics, antacids, anti-allergy agents, anti-Alzheimer's Disease agents, anti-anginal drugs, antianxiety agents, anti-arrhythmia agents, antiasthmatics, antibacterial agents, anti-bipolar agents, antifungal agents, antibiotics, anticholesterolemics, anticlotting agents, anticonvulsants, anticoagulants, antidepressants, antidiarrheal preparations, anti-emetics, antihistamines, antihyperglycemic agents, antihypertensives, anti-impotence agents, anti-infectives, anti-inflammatories, antilipid agents, antimanics, anti-migraine agents, antinauseants, antineoplastics, antiobesity agents, antiparasitics, anti-Parkinsonism agents, antipsychotics, antipyretics, antispasmodics, antistroke agents, antithrombotics, antithyroid preparations, antitumor agents, antitussives, antiulcer agents, anti-uricemic agents, antiviral agents, anxiolytic agents, appetite stimulants, appetite suppressants, autoimmune disorders agents, barbiturates, beta-blocking agents, blood glucose-lowering agents, bronchodilators, cardiovascular agents, cerebral dilators, chelating agents, cholecystekinin antagonists, chemotherapeutic agents, cholesterol-reducing agents, cognition activators, cognitive enhancers, contraceptives, coronary dilators, cough suppressants, decongestants, deodorants, dermatological agents, diabetes agents, diuretics, emollients, enzymes, erythropoietic drugs, expectorants, fertility agents, fungicides, gastrointestinal agents, growth regulators, antiheadache agents, anti-cluster headache agents, hormone replacement agents, hyperglycemic agents, hypnotic agents, hypoglycemic agents, ion-exchange resins, laxatives, migraine treatments, mineral supplements, mucolytics, narcotics, neuroleptics, neuromuscular drugs, non-steroidal anti-inflammatories (NSAIDs), nutritional additives, peripheral vasodilators, polypeptides, prostaglandins, psychotropics, renin inhibitors, respiratory stimulants, anti-restless leg syndrome agents, sedatives, steroids, stimulants, sympatholytics, thyroid preparations, tranquilizers, uterine relaxants, vaginal preparations, vasoconstrictors, vasodilators, vertigo agents, vitamins, wound healing agents, and combinations thereof.

The at least one drug is selected from the group consisting of acetazolamide, acetaminophen, acetic acid, acetohexamide, acetylsalicylic acid, buffered acetylsalicylic acid; acrivastine, acyclovir, albuterol, albuterol sulfate, alcohol, alfaxalone, alkaline phosphatase, allantoin, aloe, alprostadil, aluminum acetate, aluminum carbonate, aluminum chlorohydrate, aluminum hydroxide, alprozalam, amino acids, aminobenzoic acid, amlodipine besylate, amoxicillin, ampicillin, amsacrine, amsalog, anethole, apomorphine, ascorbic acid, aspartame, aspirin, astemizole, atenolol, atorvastatin calcium, azatidine, azatidine maleate, azithromycin, bacitracin, balsam peru, BCNU (carmustine), becampicillin hydrochloride, beclomethasone diproprionate, benzalkonium chloride, benzocaine, benzoic acid, benzophenones, benzoyl peroxide, benzquinamide, benzquinamide hydrochloride, betamethasone, bethanechol, biotin, bisacodyl, bismuth subsalicylate, bornyl acetate, bromopheniramine, bromopheniramine maleate, bupropion hydrochloride, buspirone, caffeine, calamine, calcium carbonate, calcium casinate, calcium hydroxide, camphor, captopril, carbenicillin indanyl sodium, carvedilol, cascara sagrada, castor oil, cefaclor, cefadroxil, celicoxib, cephalexin, centrizine, centrizine hydrochloride, cetirizine, cetyl alcohol, cetylpyridinium chloride, chelated minerals, chlorambucil, chloramphenicol, chlorcyclizine hydrochloride, chlordiazepoxide, chlorhexidine gluconate, chloroxylenol, chloropentostatin, chlorpheniramine, chlorpheniramine maleate, chlorpheniramine tannate, chlorpromazine, chlorpropamide, chlorthalidone, chlorzolamide, cholestyramine resin, choline bitartrate, chondrogenic stimulating protein, cimetidine, cimetidine hydrochloride, cinnamedrine hydrochloride, cinnarizine, cisapride, citalopram, citric acid, clarithromycin, clemastine, clemastine fumarate, clonidine, clonidine hydrochloride, clorfibrate, cocoa butter, cod liver oil, codeine, codeine fumarate, codeine phosphate, cortisone acetate; cotrimoxazole, ciprofloxacin HCl, cyanocobalamin, cyclizine hydrochloride, cyproheptadine, cyproheptadine hydrochloride, dexmethylphenidate, danthron, dexbromopheniramine maleate, dextromethorphan, dextromethorphan hydrohalide, diazepam, dibucaine, dichloralphenazone, diclofen, alkali metal salts of diclofen, diclofenac sodium, dicumarol, digitoxin, digoxin, dihydroergotamine, hydrogenates of dihydroergotamine, mesylates of dihydroergotamine, diltiazem, dimebon, dimenhydrinate, dimethicone, dioxybenzone, diphenhydramine, diphenhydramine citrate, diphenhydramine hydrochloride, divalproex, alkali metal salts of divalproex, docusate calcium, docusate potassium, docusate sodium, donepezil, doxazosin, doxepin, doxepin hydrochloride, doxycycline hydrate, doxylamine succinate, dronabinol, echinomycin, econazole, efaroxan, enalapril, enalaprilic acid, enoxacin, ephedrine, epinephrine bitartrate, ergotamine, ergotamine tartrate, erythromycin, erythropoietin, estropipate, ethinyl estradiol, etomidate, eucalyptol, famotidine, fenoprofen, metal salts of fenoprofen, ferrous fumarate, ferrous gluconate, ferrous sulfate, fluconazole, fluoxetine, fluoxymesterone, folic acid, fosphenytoin, 5-fluorouracil (5-FU), fluoxetine, fluoxetine hydrochloride, flurbiprofen, fluspirilene, furosemide, gabapentan, gentamicin, gemfibrozil, glipizide, glycerine, glyceryl stearate, granisetron, granisetron hydrochloride, griseofulvin, guafenesin, hexylresorcinol, hydrochlorothiazide, hydrocodone, tartrates of hydrocodone, hydrocortisone, hydrocortisone acetate, 8-hydroxyquinoline sulfate, hydroxyzine, hydroxyzine pamoate, hydrochloride salts of hydroxyzine, ibuprofen, indomethacin, inositol, insulin, iodine, ipecac, iron, iroxicam, isosorbide, monoand dinitrates of isosorbide, isoxicam, kaolin, ketamine, ketanserin, ketoprofen, lactic acid, lanolin, L-DOPA, lecithin, leuprolide acetate, levocabastine, lidocaine, lidocaine hydrochloride, lifinopril, liotrix, lisinopril, lomustine, loperamide, loratadine, lovastatin, magnesium carbonate, magnesium hydroxide, magnesium salicylate, magnesium trisilicate, meclizine, meclizine hydrochloride, mefenamic acid, meclofenamic acid, meclofenamate sodium, medroxyprogesterone acetate, meloxicam, memantine, methenamine mandelate, menthol, meperidine hydrochloride, metaproterenol sulfate, methanstenolone, methscopolamine, nitrates of methscopolamine, methsergide, methsergide maleate, methyl nicotinate, methyl salicylate, methyl cellulose, methsuximide, 17-methyltestosterone, metoclopramide, halides of metoclopramide, hydrates of metoclopramide, metronidazole, metronidazole hydrochloride, metoprolol, metoprotol tartrate, mianserin, miconazole nitrate, mineral oil, minocycline, minoxidil, mioflazine, morphine, nadolol, naproxen, sodium salts of naproxen, alkali metal salts of naproxen, nifedipine, neomycin sulfate, niacin, niacinamide, nicotine, nicotinamide; nimesulide; nitroglycerine; nonoxynol-9; norethindrone and its acetate; nystatin, octoxynol, octoxynol-9, octyl dimethyl PABA, octyl methoxycinnamate, omega-3 polyunsaturated fatty acids, omeprazole, ondansetron, ondansetron hydrochloride, oxfendazole, oxolinic acid, oxybenzone, oxtriphylline, para-aminobenzoic acid (PABA), padimate-O, paramethadione, paroxetine, penfluridole, penicillin G, pentastatin, peppermint oil, pentaerythritol tetranitrate, pentobarbital sodium, perphenazine, phenelzine sulfate, phenindamine, phenindamine tartrate, pheniramine maleate, phenobarbital, phenol, phenolphthalein, phenylephrine, tannates of phenylephrine, hydrochlorides of phenylephrine, phenylpropanolamine, phenylpropanolamine hydrochloride, phenyloin, pirmenol, piroxicam, salts of piroxicam, polymicin B sulfate, potassium chloride, potassium nitrate, pramipexole, pramiracetin, pramoxine, pramoxine hydrochloride, prazepam, prazosin, prednisolone, procainamide hydrochloride, procaterol, promethazine, promethazine hydrochloride, propoxyphene, propoxyphene hydrochloride, napsylate, prochlorperazine, prochlorperazine maleate, propanolol, propanolol hydrochloride, promethazine, promethazine hydrochloride, propanolol, prostacyclin, pseudoephedrine, sulfates of pseudoephedrine, hydrochlorides of pseudoephedrine, pyridoxine, pyrolamine, hydrochlorides of pyrolamine, tannates of pyrolamine, quetiapine, quinapril, quinidine gluconate, quinidine sulfate, quinestrol, ralitoline, ramipril, ranitidine, resorcinol, retinol, riboflavin, rivastigmine, rosiglitazone, salicylic acid, scopolamine, sertraline, sesame oil, shark liver oil, sildenafil citrate, simethicone, sodium bicarbonate, sodium citrate, sodium fluoride, sodium monofluorophosphate, spiramycin, spironolactone, sucralfate, sulfanethoxazole, sulfasalazine, sulfur, sulpiride, sumatriptan, sumatriptan succinate, tacrine, tacrine hydrochloride, terconazole, terfenadine, testosterone, tetracycline, tetracycline hydrochloride, tetrahydroaminoacridine, theophylline, thiabendazole, thiethylperazine, thiethylperazine maleate, thioperidone, thiothixene hydrochloride, timolol, timolol maleate, tolmetin, tolnaftate, topiramate, tramadol, tretinoin, triazolam, trimetrexate, trimazosin, triclosan, trimethobenzamide, trimethobenzamide hydrochloride, tripelennamine, tripelennamine hydrochloride, tripolidine hydrochloride, troleandomycin, tubulazole, undecylenic acid, valdecoxib, vancomycin, venlafaxine, verapamil HCl, vidaribine phosphate, virazole, vitamin A, vitamin C, vitamin D, vitamin B1, vitamin B2, vitamin B3, vitamin B4, vitamin B5, vitamin B6, vitamin B7, vitamin B9, vitamin B12, vitamin E, vitamin K, witch hazel, xylometazoline hydrochloride, zinc, zinc sulfate, zinc undecylenate, ziprasidone, zolpidem, salts thereof, and combinations thereof.

In yet further embodiments, the biologically active agents, pharmaceutical agents, and drugs discussed above may be incorporated inside capsules 40, 140, 240, 340 while an adhesive material may also be included in capsules 40, 140, 240, 340. Depending on the chemical and/or physical properties of the adhesive material located inside capsule 40, once the capsule is pierced by a fastener, for example, the adhesive material will eventually harden and secure fasteners, such as fasteners 60a, 60b with respect to nail 20, for example, thus securing nail 20 within the canal of the patient's femur. Preferably, once the adhesive material has hardened, fasteners 60a, 60b, for example, are prevented from backing-out of nail 20. The hardened adhesive also aids in the angular stability of a fastener in an aperture of nail 20.

Various additives may be included in the inventive adhesive to adjust its property. For example, bone cements, proteins, osteoinductive and/or osteoconductive materials, X-ray opacifying agents, supporting or strengthening filler materials, crystal growth adjusters, viscosity modifiers, pore forming agents, and other additives and a mixture thereof may be incorporated without departing from the scope of this invention.

The nature of the compounds and functional materials present in the bone cements is not limited to the heretofore described ingredients, but to the contrary, any other suitable osteoconductive, bioactive, bioinert, or other functional materials may be used in conjunction with the invention. When used, these optional ingredients, may be present in any amounts suitable for their intended purposes.

In some embodiments, the bone cement includes an osteoinductive protein, by which is contemplated any protein that is useful in assisting in or inducing bone formation. Osteoinductive proteins are deemed particularly suitable for use in conjunction with the carboxyl/calcium cement systems because, at least for many known osteoinductive proteins, such proteins may denature at an alkaline pH.

Another optional ingredient is a filler, such as a radio opaque filler. The radio opaque filler may, for instance, be a suitable bismuth, barium, or iodide compound, such as barium sulfate or bismuth hydroxide. Other suitable fillers include bioglass, silicas, alumina, biphasic calcium phosphate, calcium silicate, calcium sulfate, granular calcium phosphate ceramics, Portland cement, and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for releasing a material at a surgical site comprising:
   an implant having at least one recess therein, the at least one recess extending along at least a portion of a central longitudinal axis of the implant and forming an internal circular wall having an axis collinear with the central longitudinal axis of the implant;
   a capsule having a casing housing the material, the capsule being received and housed within the at least one recess of the implant, the capsule lying adjacent at least a portion of the internal circular wall of the at least one recess; and a piercing member having an end portion,
wherein the implant further includes an aperture in communication with the internal circular wall of the at least one recess such that a longitudinal axis of the aperture intersects the central longitudinal axis of the implant, and in that the piercing member is insertable into the aperture and the end portion of the piercing member is configured to pierce the casing of the capsule to release the material housed therein.

2. The system of claim 1, wherein the piercing member is a fastener.

3. The system of claim 2, wherein the fastener is a bone screw.

4. The system of claim 1, wherein the material includes a therapeutic agent.

5. The system of claim 4, wherein the material further includes an adhesive adapted to secure the piercing member in the at least one recess of the implant upon the adhesive hardening after first being released from the capsule.

6. An implant for housing a therapeutic capsule comprising:
an elongate shaft having a longitudinal bore at least partially therethrough a central longitudinal axis thereof, the longitudinal bore forming an internal circular wall having an axis collinear with the central longitudinal axis of the elongate shaft, the elongate shaft further having first and second bone screw receiving apertures, the apertures each extending transverse to the longitudinal bore and are in communication with the internal circular wall of the longitudinal bore such that a longitudinal axis of each of the apertures intersects the longitudinal axis of the internal circular wall of the longitudinal bore,
wherein the therapeutic capsule having a casing housing a therapeutic agent is positioned within the bore and lies adjacent at least a portion of the internal circular wall of the longitudinal bore and communicates with both the first and second apertures.

7. The implant of claim 6, further comprising:
a holder adapted to be received within the longitudinal bore of the elongate shaft, the holder adapted to receive the therapeutic capsule therein and position the capsule at least partially within the first and second apertures such that the capsule communicates with both the first and second apertures.

8. The implant of claim 6, further comprising:
a holder adapted to be received within the longitudinal bore of the elongate shaft, wherein the holder has a first and a second end, each end having a recess for holding a therapeutic capsule to position the capsule at least partially within either the first or the second apertures.

9. The implant of claim 8, wherein the internal circular wall of the longitudinal bore is threaded adjacent the first and second apertures and the holder is threaded and adapted to threadingly engage the threaded internal circular wall of the longitudinal bore of the elongate shaft.

10. The implant of claim 9, wherein the therapeutic capsule also includes an adhesive.

11. The implant of claim 9 further comprising:
a first therapeutic capsule; and
a second therapeutic capsule;
wherein the holder is adapted to receive both first and second therapeutic capsules therein and position the first capsule at least partially within the first aperture and the second capsule at least partially within the second aperture.

12. The implant of claim 11, wherein the first and second therapeutic capsules also each include an adhesive.

13. A bone nail comprising:
an elongate shaft having a longitudinal axis extending from a proximal end to a distal end of the shaft, the shaft having a plurality of fastener receiving apertures having a longitudinal axis transverse to the longitudinal axis of the shaft, and at least one recess forming an internal circular wall that communicates with each fastener receiving aperture, the at least one recess having a central longitudinal axis collinear with the longitudinal axis of the shaft such that the longitudinal axis of each of the fastener receiving apertures intersects the central longitudinal axis of the at least one recess;
at least one therapeutic capsule having a casing housing a therapeutic agent; and
a holder adapted to be received at least partially within the at least one recess of the elongate shaft such that the holder lies adjacent the internal circular wall of the at least one recess, the holder having at least one recess that receives the capsule and positions the capsule at least partially within at least one of the plurality of fastener receiving apertures.

14. The bone nail of claim 13, wherein the capsule also includes an adhesive.

15. The bone nail of claim 13, wherein the holder is cylindrical.

16. The bone nail of claim 13, wherein the holder is threaded and the internal circular wall of the at least one recess of the elongate shaft is threaded and the holder is adapted to threadingly engage the internal circular wall of the at least one recess.

17. The bone nail of claim 13, wherein the bone nail has first and second transverse apertures and the holder is positioned within the internal circular wall of the at least one recess such that the holder communicates with the first and second transverse apertures, the holder having first and second recesses each adapted to receive a capsule.

18. The bone nail of claim 17, wherein a first capsule is positioned at least partially within the first transverse aperture and the second capsule is positioned at least partially within the second transverse aperture.

19. The bone nail of claim 18, wherein the first and second capsules also each include an adhesive.

20. A method for regulating the release of a therapeutic agent to an implant, the method comprising:
positioning the implant adjacent bone, the implant having at least one aperture for receiving an elongate fastener therein and a recess forming an internal circular wall that communicates with the aperture, the recess extending along at least a portion of a central longitudinal axis of the implant such that a longitudinal axis of the aperture intersects the central longitudinal axis of the implant;
placing a therapeutic capsule within the recess, the capsule extending at least partially into the at least one aperture, the capsule having a casing housing the therapeutic agent, the casing configured to be pierced by a fastener;
inserting the fastener through the at least one aperture; and
piercing the capsule with at least a portion of the fastener such that the therapeutic agent is released from the capsule adjacent the location of the at least one aperture on the implant.

21. The method of claim 20, wherein the implant is an intramedullary nail.

22. The method of claim 21, wherein the recess is a longitudinal bore extending at least partially along a length of the intramedullary nail.

23. The method of claim 22, further comprising:

placing a retaining ring around the casing of the capsule prior to piercing the capsule with the fastener, the retaining ring configured to aid in maintaining the position of the adhesive capsule within the longitudinal bore of the intramedullary nail.

24. The method of claim 20, wherein the implant has a plurality of apertures adapted to each receive an elongate fastener therein and a recess forming an internal circular wall that communicates with each aperture, the method further comprising:

placing a capsule within the recess communicating with each aperture, wherein each capsule extends at least partially into each aperture.

* * * * *